US008962020B2

(12) United States Patent
Cohen et al.

(10) Patent No.: US 8,962,020 B2
(45) Date of Patent: Feb. 24, 2015

(54) LONG-ACTING AND CONTROLLED RELEASE FORMULATIONS OF 2-[(3-CHLOROPHENYL) AMINO] PHENYLACETIC ACID

(75) Inventors: Margo P. Cohen, New York, NY (US); Clyde W. Shearman, Westchester, PA (US)

(73) Assignee: Glycadia Inc., Philadelphia, PA (US)

( * ) Notice: Subject to any disclaimer, the term of this patent is extended or adjusted under 35 U.S.C. 154(b) by 0 days.

(21) Appl. No.: 13/559,282

(22) Filed: Jul. 26, 2012

(65) Prior Publication Data

US 2014/0030325 A1    Jan. 30, 2014

(51) Int. Cl.

| | | |
|---|---|---|
| *A61K 9/28* | (2006.01) | |
| *A61K 9/00* | (2006.01) | |
| *A61K 31/195* | (2006.01) | |
| *A61P 3/10* | (2006.01) | |
| *A61K 9/16* | (2006.01) | |
| *A61K 9/50* | (2006.01) | |

(52) U.S. Cl.
CPC ............. *A61K 9/1623* (2013.01); *A61K 9/5026* (2013.01)
USPC ............................ 424/465; 424/400; 514/567

(58) Field of Classification Search
USPC ........................................................ 424/450
See application file for complete search history.

(56) References Cited

U.S. PATENT DOCUMENTS

| | | | | | |
|---|---|---|---|---|---|
| 4,968,505 | A | * | 11/1990 | Okada et al. ................. | 424/400 |
| 5,133,974 | A | * | 7/1992 | Paradissis et al. ............ | 424/480 |
| 5,164,193 | A | * | 11/1992 | Okada et al. ................. | 424/468 |
| 5,576,022 | A | * | 11/1996 | Yang et al. .................... | 424/472 |
| 6,355,680 | B1 | * | 3/2002 | Cohen ........................... | 514/534 |
| 6,552,077 | B2 | * | 4/2003 | Cohen ........................... | 514/534 |
| 2007/0110806 | A1 | * | 5/2007 | Yoshitake et al. ............ | 424/470 |
| 2008/0255236 | A1 | * | 10/2008 | Cohen et al. ................. | 514/567 |
| 2010/0221356 | A1 | * | 9/2010 | Kidane et al. ................ | 424/499 |

FOREIGN PATENT DOCUMENTS

| | | |
|---|---|---|
| CA | 2378456 A1 | 9/2002 |
| EP | 1242069 A2 | 9/2002 |
| JP | 4833468 B2 | 12/2011 |
| KR | 100817443 B1 | 10/2007 |
| WO | WO 2008/050987 * | 5/2008 |
| WO | WO-2009-024858 * | 2/2009 |
| WO | WO-2009-133141 * | 11/2009 |

OTHER PUBLICATIONS

Hypromellose. (2007). In Dorland's Illustrated Medical Dictionary. Retrieved from http://www.credoreference.com/entry/ehsdorland/hypromellose.*
Zero-order reaction. (2009). In the Penguin Dictionary of Science. Retrieved from http://www.credoreference.com/entry/penguinscience/zero_order_reaction.*
Cohen MP, Evidence linking glycated albumin to altered glomerular nephrin and VEGF expression, proteinuria, and diabetic nephropathy, Kidney International, 68 (2005), 1554-1561.*
Cohen, Margo P. et al., Inhibiting albumin glycation attenuates dysregulation of VEGFR-1 and collagen IV subchain production and the development of renal insufficiency, Am J Physiol Renal Physiol, 2007 (1st pub Oct. 3, 2006), F789-F795, Vol-Issue 292, American Physiological Society, MD US, (doi:10.1152/ajprenal.00201.2006).
Cohen, Margo P. et al., Inhibiting albumin glycation in vivo ameliorates glomerular overexpression of TGF-1, Kidney International, 2002, pp. 2025-2032, vol. 61, International Society of Nephrology.
Cohen, Margo P. et al., Evidence linking glycated albumin to altered glomerular nephrin and VEGF expression, proteinuria, and diabetic nephropathy, Kidney International, 2005, pp. 1554-1561, vol. 68, International Society of Nephrology.

* cited by examiner

*Primary Examiner* — Frederick Krass
*Assistant Examiner* — Celeste A Roney

(57) ABSTRACT

Formulation of long-acting and controlled release preparations of 2-[(3-chlorophenyl)amino] phenylacetic acid (23CPPA) are disclosed. Long-acting preparations comprise a slow-release formulation coated onto a pharmaceutical composition containing 23CPPA, protect against gastric irritation, slow 23CPPA absorption, extend release of 23CPPA, protect against excessively high 23CPPA blood concentrations, and prolong maintenance of blood concentrations of 23CPPA after administration. Controlled release formulations comprise (a) a core element which is a compressed tablet containing a therapeutic dose of 23CPPA and an amount of a solubility modulating substance that controls the release of said 23CPPA in order to provide a therapeutic level over a period of about 24 hours; and (b) on the outer surface of the core element, a sufficient amount of an enteric coating that causes the 23CPPA to release at a rate that permits the use of once-a-day dosing to maintain steady state therapeutic levels of 23CPPA.

11 Claims, 2 Drawing Sheets

LONG-ACTING AND CONTROLLED RELEASE FORMULATIONS OF 2-[(3-CHLOROPHENYL) AMINO] PHENYLACETIC ACID

FIELD OF INVENTION

The present invention is directed to long-acting coated and controlled release unit dose formulations of 2-[(3-chlorophenyl)amino] phenylacetic acid (23CPPA) for the treatment of glycation-related complications of diabetes.

BACKGROUND OF THE INVENTION

The present invention is directed to long-acting coated and controlled release unit dose formulations of 2-[(3-chlorophenyl)amino] phenylacetic acid (23CPPA) for the treatment of glycation-related complications of diabetes. More particularly, it has been discovered that intestinal absorption of the drug is necessary to preclude gastric irritation and accelerated absorption leading to high blood levels in excess of therapeutic concentrations, that the desired therapeutic concentration of 23CPPA that meets drug-to target relationships is in the range of only 10% of that predicted by stoichiometric relationships, that only a small fraction of the albumin in the circulation undergoes nonenzymatic glycation during a 24 hour period, that maintenance of therapeutic blood levels after oral administration of 23CPPA is achieved in extended release pharmaceutical dosage forms, and that long-acting and controlled release unit dose formulations provide delivery of blood concentrations of the drug that are in the therapeutic range of 5,000 to 20,000 ng/ml and that meet drug-to-target relationships with respect to the rate of nonenzymatic glycation of albumin.

The present invention provides formulations of 23CPPA that deliver the compound for absorption in the intestine, that slow and extend the release of 23CPPA, that retard absorption and prolong residence time of 23CPPA in the circulation, and that deliver blood concentrations of the drug that are in the therapeutic range. The present invention also provides once-a-day formulations of 23CPPA that comprise a tablet formulation with an enteric coating that deliver the compound over an extended period of time along the length of the intestinal tract. As used herein, the term 23CPPA includes the free base form and pharmaceutically acceptable salts of 23CPPA such as 23CPPA potassium salt.

23CPPA is an anti-glycation agent that impedes the condensation of free glucose with albumin in a reaction known as nonenzymatic glycation, thereby decreasing the formation of albumin modified by Amadori glucose adducts (U.S. Pat. No. 6,355,680). 23CPPA lowers the concentration of albumin modified by Amadori glucose adducts, even in the presence of marked hyperglycemia, and lessens the pathophysiologic effects of Amadori-modified glycated albumin (AGA) in living organisms (Cohen et al, Kid Int 61:2025-2032, 2002; 68:1554-1566, 2005; AJP Renal 292:789-795, 2007). Experimental studies have causally linked elevated concentrations of albumin modified by Amadori glucose adducts to the pathogenesis of diabetic kidney disease, and have shown that inhibiting the formation of AGA with 23CPPA ameliorates the structural and functional changes associated with diabetic nephropathy and the development of renal insufficiency (Cohen et al, Kid Int 61:2025-2032, 2002; 68:1554-1566, 2005; AJP Renal 292:789-795, 2007), demonstrating that this compound is useful in the treatment of this condition and in arresting progression to renal failure.

23CPPA does not have the molecular formula of a nonsteroidal anti-inflammatory drug (NSAID), and is not an isomer or enantiomer of a NSAID, which are drugs that inhibit the cyclooxygenase (COX) enzymes COX-1 and COX-2. Because 23CPPA is not a pharmacologic inhibitor of the COX-1 or COX-2 enzymes, it does not have the ulcerogenic properties that arise from the COX enzyme inhibitory activity of NSAIDs and is not expected to cause gastric irritation or ulcerogenesis. However, since the pKa (logarithm of the acid dissociation constant) of pharmaceutically acceptable salts of 23CPPA such as potassium is 4.0, hydrogen replaces the potassium at the lower pH that prevails in the intense acid environment of the stomach and the compound becomes a carboxylic acid, which can cause local irritation to the stomach. The acid environment of the stomach also can cause 23CPPA to precipitate out of solution and come into direct and concentrated contact with the stomach lining and cause irritation. The unexpected demonstration that 23CPPA exhibits properties of gastric irritation make it desirable, as disclosed in the present invention, to bypass the stomach in delivery of the drug to the circulation by oral administration.

23CPPA relies on interaction with albumin in the circulation to effectuate its anti-glycation activity, and does not require stoichiometric concentration ratios of drug-to-enzyme for therapeutic efficacy as do the NSAIDs. However, since the concentration of albumin in the blood is approximately 4.5 grams per deciliter liter and the plasma volume is approximately 4 liters, representing a total of approximately 2600 micromoles of albumin in the circulation at a concentration of 660 nmoles per milliliter, it would be expected that on a molar basis an amount of 23CPPA at least equivalent to the amount of albumin would be required to fill the sites with which 23CPPA interacts. However, the unexpected finding that about 10% of that amount is sufficient to fill available sites which interact with 23CPPA enables development of formulations that deliver into the circulation lesser but nevertheless clinically effective concentrations of 23CPPA during an extended period of time.

Since 23CPPA interacts with plasma albumin to effectuate anti-glycation activity, it would be expected that a concentration of drug equivalent to the circulating concentration of albumin and/or glucose would be required in impede the condensation of free glucose with the albumin protein. However, the unexpected finding that less than one percent of circulating albumin is nonenzymatically glycated during a 24 hour period, even at glucose concentrations eight-fold higher than the physiologic range such as can be found in people with diabetes, enables development of long-acting and controlled release dosage formulations that can deliver blood concentrations of 23CPPA over a 24 hour period that match drug-to target relationships with respect to the rate of nonenzymatic glycation of albumin during that period of time.

The present invention therefore addresses the existing need for preparations of 23CPPA that are capable of eliciting the desired effect in the safest and most efficacious manner and that deliver the drug over a period compatible with clinical requirements by the disclosure of preparations of 23CPPA that achieve these aims by delivering the drug to the intestinal tract, slowing its dissolution, extending its release over a prolonged period of time, and delivering concentrations of the drug to the blood that meet drug-to-target relationships with respect to sites available for binding to 23CPPA.

Additionally, the formulations of the present invention avoid patient non-compliance with omission of prescribed dosings necessary for optimum clinical control attendant to the nuisance of multiple daily dosings.

SUMMARY OF THE INVENTION

It is an object of the present invention to provide methods to deliver the compound 23CPPA for absorption in the intestinal tract without direct concentrated contact with the stomach lining.

It is another object of the present invention to provide methods to deliver 23CPPA without precipitation of the compound resulting from the acidic environment of the stomach.

It is also an object of the present invention to preclude rapid absorption that can give rise to unexpected and unnecessarily high blood concentrations of 23CPPA.

Another object of the invention is to provide methods of delivery of 23CPPA that result in blood concentrations that are in the desired therapeutic range.

It is also an object of the invention to provide methods to slow the absorption and prolong the release of 23CPPA in the intestinal tract.

It is yet another object of the invention to retard the absorption and extend the residence time of 23CPPA in the circulation.

A further object of the present invention is to provide formulations of 2-[(3-chlorophenyl)amino] phenylacetic acid and its pharmaceutically acceptable salts that deliver the compound over an extended period of time along the length of the intestinal tract.

Another object of the present invention to provide methods of delivery of 23CPPA to the blood in clinically sufficient amounts over a twenty four hour period.

It is also an object of the present invention to provide methods of delivery of 23CPPA in controlled release unit dose formulations that can be administered once a day by the oral route.

Another object of the invention is to provide methods for delivery of blood concentrations of 23CPPA that are in the therapeutic range and that meet drug-to-target relationships with respect to the rate of nonenzymatic glycation of albumin over a twenty four hour period.

It is a further object of the present invention to provide a once-a-day 23CPPA dosage system which has a substantially zero order release dissolution profile of 23CPPA.

It is also an object of this invention to provide a once-a-day 23CPPA dosage system that releases 23CPPA at a rate that maintains steady state therapeutic levels of 23CPPA.

It is yet another object of this invention to provide a once-a-day 23CPPA dosage system which provides a blood concentration of 23CPPA from about 5,000 to 20,000 ng/ml.

It is a further object of the present invention to provide a once-a-day 23CPPA dosage system that maintains therapeutic levels but avoids high plasma levels of 23CPPA arising from rapid absorption in the upper gastrointestinal tract.

These and other objects of the invention are achieved by providing long-acting formulations of 23CPPA and pharmaceutically acceptable salts thereof. These formulations are suitable for administration by the oral route, protect against exposure of the gastric lining to concentrated contact with the drug, and deliver the drug for absorption from the intestinal tract of clinically sufficient amounts over a prolonged period of time.

These and other objects of the invention are further achieved by providing methods and compositions of 23CPPA and pharmacologically acceptable salts thereof for protecting against gastric irritation, slowing absorption, controlling the rate of release, decreasing the peak concentration, and maintaining the blood concentrations of 23CPPA for prolonged periods of time.

These and other objects of the invention are enabled by the novel finding that buffering agents protect against gastric irritation resulting from precipitation of the compound in the stomach whilst providing a clinically acceptable rate of onset of the pharmaceutical product from the intestinal tract.

These and other objects of the invention also are enabled by the novel and unexpected finding that saturation of available binding sites for in the albumin molecule for interaction with 23CPPA can be achieved with plasma concentrations of drug that are less than that predicted stoichiometrically by the plasma concentration of albumin.

These and other objects of the invention are further achieved by providing methods and compositions of once-a-day controlled release 23CPPA formulations which comprise: (a) a core element comprising a compressed tablet that contains a therapeutic dose of 23CPPA and an amount of a solubility modulating substance which is sufficient to control the release of said 23CPPA to provide a therapeutic level over a period of about 24 hours; and (b) a sufficient amount of a substantially uniform enteric coating which is placed around said core element.

These and other objects of the invention are also achieved by providing a dosage form of 23CPPA with various release rate profiles in various pH dissolution media for the drug substance and which are a substantially zero order release rates.

These and other objects of the invention are enabled by the novel finding that nonenzymatic glycation of albumin proceeds at a steady and relatively slow rate of 0.005 to 0.008 percent per day per mM glucose concentration.

These and other objects, features and advantages of the present invention become more readily apparent from the descriptions and examples that follow in the detailed description of the invention and examples. Other features of the invention will become apparent in the course of the following description of the exemplary embodiments which are given for illustration of the invention and are not intended to be limiting thereof.

DETAILED DESCRIPTION OF THE INVENTION AND PREFERRED EMBODIMENTS

Figure 1:
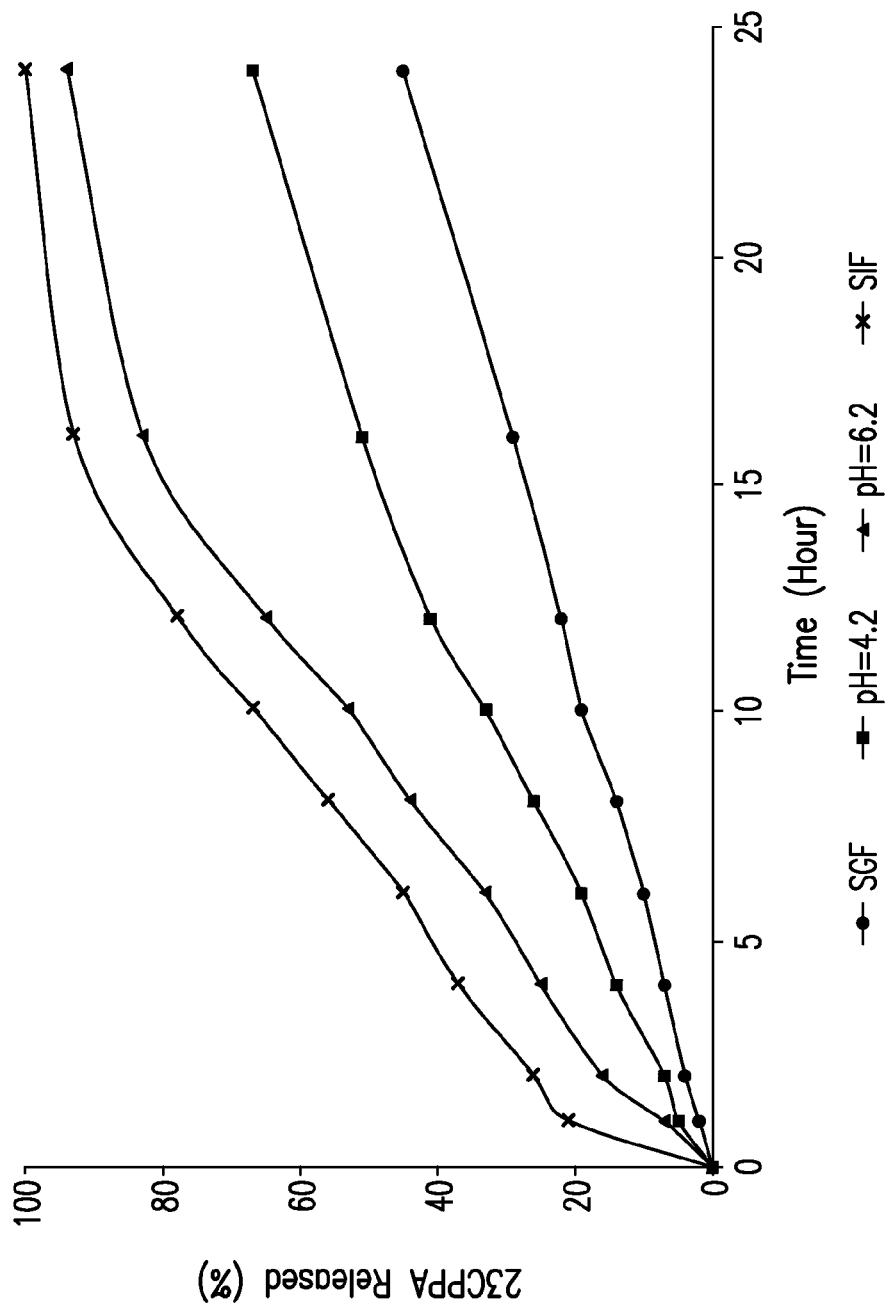
FIG. 1 is a graph of the dissolution profile of a 1000 mg 23CPPA tablet made according to Example 11 of the present application in simulated gastric fluid (SGF), pH 4.2, pH 6.2 and simulated intestinal fluid (SIF).

The present invention provides formulations of long-acting preparations of 23CPPA and pharmaceutically acceptable salts. The preparations comprise a 23CPPA component which is prepared by combining or coating with a formulation containing components that prolong or extend release of the active pharmaceutical ingredient. The formulations provide protection from gastric irritation, slow absorption of the 23CPPA component, prolong release of 23CPPA from the preparation, decrease the peak concentration of 23CPPA in the blood, and slowly deliver to the blood sufficient concentrations of 23CPPA during a prolonged period after administration. The risk of side effects is reduced and patient compliance is enhanced by decreasing the need for frequent administration of the drug.

The present invention also provides formulations of controlled release preparations of 23CPPA and pharmaceutically acceptable salts. The formulations comprise a core element comprising a compressed tablet that contains a therapeutic dose of 23CPPA and an amount of a solubility modulating substance which is sufficient to control the release of said 23CPPA to provide a therapeutic level over a period of about 24 hours, and a sufficient amount of a substantially uniform enteric coating which is placed around said core element.

The long-acting preparations of 23CPPA of this invention deliver clinically effective concentrations that meet drug-to-target relationships during the period of time that the drug is in the circulation.

The controlled release formulations of 23CPPA of this invention deliver steady state plasma levels of 23CPPA sufficient to permit once-a-day dosing.

The controlled release formulations of 23CPPA of this invention take into account the biological principle of first pass effect and the correspondent absolute bioavailability of 23CPPA, which is calculated from oral compared to intravenous administration and is an important determinant of the amount of drug substance necessary to provide therapeutic plasma levels of 23CPPA in a once-a-day dosing.

The once-a-day formulations of the present invention deliver clinically effective concentrations of 23CPPA that meet drug-to-target relationships over a period of 24 hours according to the albumin concentration in the blood (approximately 600 nmoles per ml) and the rate of reaction between free glucose and albumin, which proceeds slowly and continuously. The proportion of circulating albumin undergoing nonenzymatic glycation during a 24 hour period, measured in the presence of increasing glucose concentrations representative of those observed in patients with diabetes, was found to be unexpectedly low at steady state levels between 0.005 to 0.008 percent per mM glucose per day. Steady state plasma levels achieved with once-a-day dosing of 500 to 1000 mg of 23CPPA (molecular weight=300) can effectively inhibit nonenzymatic condensation of glucose with albumin.

These and other objects and embodiments of the invention are clarified in the descriptions and examples provided hereinafter.

In this invention, long-acting formulations are prepared by mixing, layering or coating 23CPPA with a formulation containing components that prolong and extend absorption of 23CPPA from the intestinal tract.

In this invention, long-acting formulations are prepared by mixing, layering or coating 23CPPA with a formulation containing water insoluble components that prevent absorption of the 23CPPA component in the stomach.

In this invention, long-acting formulations are prepared by mixing, layering or coating 23CPPA with a formulation containing intestinally soluble components that slow and sustain the release of 23CPPA in the gastrointestinal tract.

In this invention, the long-acting pharmaceutical composition comprising 23CPPA, a buffering agent, a lubricant or other additives, and a diluent, contains at least 2 parts by weight, especially preferably 2-50 parts by weight, of buffering agent per 100 parts by weight of 23CPPA.

In this invention, buffering agents are important for protection against the acidic environment of the stomach and to provide a suitable rate of onset for the final pharmaceutical product. The buffering agent controls the pH of the formulation when dissolved, and preferably yields a pH>6.8, 7.0, 7.2, or 7.4 and <7.8, 7.7, or 7.6, when mixed with 50 ml or 100 or 200 ml of water at 25° C. Buffering agents which can be used are alkali metal phosphates, carbonates and bicarbonates and these agents are preferably employed in a weight ratio relative to 23CPPA of greater than about 1:5, 2:5, 2:1, 3:1, or 5:1. In a preferred embodiment, the buffer-to-23CPPA weight ratio ranges from 1:5 to about 4:5. Preferred alkali metal carbonates and bicarbonates are sodium and potassium. Buffering agents can be used singly, as well as mixtures of two or more of these agents.

Diluents or filler excipients are preferably added to increase the resulting dosage units bulk and to improve blending characteristics. Freely soluble diluents are particularly preferred because they improve the solubility of the final product. The diluent preferably has a solubility in water at 25° C. of greater than about 10, 15, or 20 g/100 ml of water. A particularly preferred diluent is mannitol, which is substantially non-hygroscopic, and which has a solubility in water of 22 g/100 ml. Other suitable diluents include lactose, glucose, sucrose, xylitol, and especially lactilol monohydrate due to its beneficial non-hygroscopic properties.

In the preparation of long-acting 23CPPA component of this invention, a pharmaceutical composition containing 23CPPA, diluents, and buffering agents, and, optionally, suitable additives is microencapsulated by a conventional method. Alternatively, this pharmaceutical composition as is, or after the addition of suitable additives such as binders, lubricants, disintegrators, vehicles, disintegration retarding agents, plasticizers, coloring agents, flavors, and the like, is formed into tablets, granules, fine granules, beads, or the like according to conventional methods. Then, a sustained-release coat is applied onto them.

Any compounds conventionally used as a sustained-release coat can be used for the purpose of this invention. Specific examples which can be given include water insoluble polymers such as ethylcellulose, aminoalkyl methacrylate copolymer, polyvinyl acetate, polyvinyl chloride, polyethylene, and the like; intestinally soluble polymers such as cellulose acetate phthalate, hydroxypropyl methylcellulose phthalate, hydroxypropyl methylcellulose acetate succinate, carboxymethylethylcellulose, styrene acrylic acid copolymer, methacrylic acid copolymer, maleic anhydrous acid copolymer, shellac, and the like; paraffin waxes such as paraffin, microcrystalline wax, and the like; higher alcohols such as stearyl alcohol, cetyl alcohol, and the like; higher fatty acid esters such as glycerine fatty acid esters, hydrogenated oils, carnauba wax, beeswax, Japan (haze) wax, and the like; and higher fatty acids such as stearic acid, palmitic acid, myristic acid, behenic acid, and the like (or the sodium, calcium or magnesium salts of these higher fatty acids). Among these, preferable compounds are water insoluble polymers and intestinally soluble polymers which are soluble in water at an acidity level in the range of about pH 5.5-7.1, especially of about 7.

The above compounds may be used as a sustained-release coat either individually or in combination. Other compounds may also be formulated into sustained-release coats. Given as examples of ideal sustained-release coats are an intestinally soluble coat comprising 1 part by weight of methacrylic acid copolymer S (methacrylic acid-methyl methacrylate copolymer containing 25.0-34.5% of methacrylic acid on dry basis; trade name: Eudragit S), 0.03-0.3 part by weight of glycerine fatty acid ester, and 0.01-1.5 parts by weight of talc, and a water insoluble coat comprising 1 part by weight of water insoluble polymer, 0.05-0.5 part by weight of polyvinyl pyrrolidone, and 0.01-1.5 parts by weight of talc.

The long-acting pharmaceutical composition containing the 23CPPA component can be used as such or can be used after addition of suitable additives such as binders, lubricants, disintegrators or disintegration-retarding agents, coloring agents, flavors and the like Alternatively, the 23CPPA-containing pharmaceutical composition can be microencapsulated by a conventional method.

The amount of the sustained-release coat to be used varies depending on the types of preparation. Usually, an amount ranging from 1 to 80% by weight based on the amount of the pharmaceutical composition is applicable. In the case of intestinally soluble coats, an amount of 10-80% by weight, especially of 10-60% by weight, is preferable. An amount of 1-80% by weight, especially of 3-60% by weight, is preferable for water insoluble coats.

There are no specific limitations as to the types of long-acting 23CPPA preparation of this invention. It may be powders, fine granules, granules, beads, capsules, tablets, or the like.

In this invention, the core element of the controlled release formulations comprises a compressed tablet containing a therapeutic dose of 23CPPA and an amount of a solubility modulating substance which is sufficient to control the release of said 23CPPA to provide a therapeutic level over a period of about 24 hours.

In this invention, the solubility modulating substance of the controlled release formulation is preferably a hydrogel forming polymers, such as hydroxypropyl methylcellulose, hydroxypropyl cellulose, hydroxyethyl cellulose, sodium alginate, xanthan gum, carbomer, and the like, but it is possible to use other solubility modulating agents such as sodium citrate and other organic acids, and sodium chloride. In addition other pharmaceutically acceptable diluents such as lactose, dextrose, sucrose, starch, microcrystalline cellulose, dicalcium phosphate and the like can be used.

The core element is preferably manufactured by first passing all of the dry ingredients through a screen (e.g. 300 mesh USSS) and thereafter tumble blending the dry ingredients for 5 to 120 minutes to form a compressible powder blend. The compressible powder blend is preferably pressed into tablets using an automatic tabletting machine provided with a suitable die.

The core element of the controlled release formulation is coated with an enteric coating composition which in combination with the solubility modulating hydrogel provides the extended release of the 23CPPA component. As used herein and in the appended claims, the term "enteric coating" is used to define a "pH dependent" coating which will resist dissolution in the acidic medium of the stomach and will dissolve in the environment of the small intestine. The enteric coating will comprise from 1 to 10% and preferably 1 to 6% and most preferably from 2 to 4% by weight based on the combined weight of the tabletted core and the coating. The enteric coating polymer may be selected from the group consisting of shellac, methacrylic acid copolymers, (Eudragit S or L) cellulose acetate phthalate, hydroxypropylmethylcellulose phthalate, hydroxypropylmethylcellulose acetate succinate, cellulose acetate trimellitate and polyvinyl acetate phthalate. The preferred polymer is hydroxypropylmethylcellulose phthalate. The thickness of the coating is selected to provide the desired release rate which is dependent on the thickness of the coating and the particular coating.

A preferred enteric coating polymer is hydroxypropyl methylcellulose phthalate, NF (Type 200731) which is a monophthalic acid ester of hydroxypropyl methylcellulose and contains not less than 18.0 percent of methoxy groups, not less than 5.0 percent and not more than 9.0 percent of hydroxypropoxy groups, and not less than 27.0 and not more than 35.0 percent of phthalyl groups, calculated on a dry basis. Other auxiliary coating aids such as a minor amount (1-5 wt. % based on the active core component and the total weight of the final coating) of a plasticizer such as acetyltributyl citrate, triacetin, acetylated monoglyceride, rape oil, olive oil, sesame oil, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, polyethyleneglycol (molecular weight of from 380 to 420), propylene glycol and mixtures thereof in combination with an antisticking agent which may be a silicate such as talc. The antisticking agent may be added in an amount which is equivalent to 0.3 to 1.0:1.0 by weight of the enteric coating polymer. These components may be added to the enteric coating polymer in combination with appropriate solvents.

The enteric coated tablet core contains an active core which is coated with a sufficient amount of the enteric coating which will substantially maintain its integrity in the acidic region of the gastrointestinal tract. The enteric coated tablet is designed to release 23CPPA in vitro in a substantially zero order release profile in simulated intestinal fluid over a period of about 2 to 18 hours after the dosage form of the invention is placed in simulated intestinal fluid.

The tablet component of the core element of the invention may comprise:
23CPPA potassium, 15 to 60 wt. %
anhydrous lactose, NF 5 to 40 wt. %
hydroxypropyl methylcellulose, USP 20 to 42 wt. %
sodium citrate, USP 5 to 15 wt. %
colloidal silicon dioxide 0.1 to 2 wt. %

The coating suspension for a 10.5 Kg. batch of tablets may be prepared by blending:

|  | wt. % | Kg/batch |
| --- | --- | --- |
| hydroxypropyl methyl cellulose phthalate, NF | 69.0% | 0.217 |
| hydroxypropyl cellulose, NF | 3.3% | 0.011 |
| talc, USP | 20.7% | 0.065 |
| acetyl tributyl citrate | 7.0% | 0.022 |
| isopropyl alcohol, USP | 4.190 L |  |
| purified water, USP | 1.796 L |  |

A sufficient amount of the isopropyl alcohol and the purified water are added to form a coating suspension. The isopropyl alcohol and the purified water are evaporated during processing and do not appear in the final product.

The controlled release 23CPPA formulation of the present invention will preferably have a dissolution release rate, in 1000 ml of simulated intestinal fluid in a USP 23 Type II apparatus at 37° C. and 100 rpm as measured by UV at 283 nm, which substantially corresponds to the following:
a) from 0 to 35 wt. % and preferably from 5 to 30 wt. % of total 23CPPA is released after one hour;
b) from 40 to 65 wt. % and preferably from 45 to 60 wt. % total 23CPPA is released after five hours;
c) from 65 to 85 wt. % and preferably from 70 to 80 wt. % total 23CPPA is released after ten hours;
d) not less than 70% of total 23CPPA is released after sixteen hours;
e) not less than 80% of total 23CPPA is released after twenty four hours.

Simulated gastric fluid consists of 2.0 g sodium chloride; 3.2 g pepsin in 7.0 ml of hydrochloric acid (37%) and sufficient water to make 1000 ml. The pH is about 1.2. Simulated intestinal fluid consists of 6.8 g of monobasic potassium phosphate; 77 ml of 0.2N sodium hydroxide; 10 g pancreatin; and water to make 1000 ml. The term "total 23CPPA" is used to point out the measurable quantity of 23CPPA that is found when UV analysis using a Shimadzu UV spectrophotometer at 283 nm is carried out.

Generally the controlled release dosage form will contain from about 250 to 2500 mg of 23CPPA or its pharmaceutically equivalent salt which are prepared according to the given example (EXAMPLE 11) which is included to demonstrate embodiments of the invention.

The long-acting and controlled release 23CPPA preparations of this invention prepared as fully described above can limit the maximum blood concentration of 23CPPA by suppressing and controlling the rate of release of 23CPPA from the preparation, and can maintain the blood concentration of 23CPPA constant for a considerably long period of time. This reduces the risk of side-effect occurrences and, at the same time, can provide a prescription that avoids need for multiple daily dosings.

In addition to being protected from the acid environment of the stomach, the preparations of this invention are delivered in a formulation that keeps it from becoming acidic.

The long-acting and controlled release preparations of the present invention deliver concentrations of 23CPPA to the blood that meet drug-to-target relationships with respect to sites available in circulating albumin for interaction with 23CPPA.

The above disclosure generally describes the present invention. A more complete understanding can be obtained by reference to the following specific examples which are provided herein for purposes of illustration only and are not intended to limit the scope of the invention. Other features of the invention will become apparent in the course of the following description of the exemplary embodiments which also are given for illustration of the invention and are not intended to be limiting thereof.

Example 1

Pharmacokinetic and Histopathological Studies Following Oral Administration of 23CPPA in Rats Rats (Charles River Laboratories) received 23CPPA orally at dosages of 25 and 75 mg per kg per day for fourteen days. Samples were obtained at timed intervals following administration for measurement of plasma concentrations of 23CPPA and pharmacokinetic analysis, and tissue was histopathologically examined at the end termination of the study period. Induction of gastric irritation, rapid absorption with maximum plasma concentration of drug at 0.25 hours after administration, and a relatively short residence time of 23CPPA in the circulation was demonstrated.

| Dose (mg/kg/day) | Tmax hr | Half-life hr | Gastric Histo-pathology. (% animals) |
|---|---|---|---|
| 25 | 0.25 | 2.3 | Edema/inflammation (20) |
| 75 | 0.25 | 2.3 | Edema/inflammation (30) |

Example 2

Non-Stoichiometric Saturation of Albumin Binding Sites by 23CPPA

Plasma concentrations of 23CPPA were measured in samples obtained at timed intervals after oral administration of graduated doses of nonformulated 23CPPA to normal men. Peak concentrations of 23CPPA were not dose proportional and exhibited plateauing which indicated saturation of available sites in albumin at concentrations of drug approximately ten percent of the albumin concentration.

| 23CPPA (Relative Dose) | Plasma Albumin (nmole/ml) | Plasma 23CPPA (nmole/ml) |
|---|---|---|
| 1 | 676 | 7 |
| 2 | 654 | 19 |
| 5 | 662 | 44 |
| 10 | 644 | 64 |
| 15 | 651 | 70 |
| 20 | 644 | 74 |

Example 3

3A. Preparation of Non-Coated Granules for Long-Acting Formulations 1,000 g of 23CPPA, 100 g of sodium carbonate, and 100 g of sodium bicarbonate are mixed and pulverized. The fine powders thus produced are processed to produce spherical granules, using 600 g of purified mannitol that is obtained by shifting through 20-28 mesh as a core, while spraying a solution of 25 g of hydroxypropyl cellulose in 475 g of ethyl alcohol. The granules are then dried for 3 hours at 55° C. These dried granules are then passed through a 14 mesh followed by passage through a 28 mesh. The granules which do not go through the 28 mesh are taken as non-coated granules. The formulation of the non-coated granules is as follows:

| Component | % by weight |
|---|---|
| 23CPPA | 54.8 |
| Sodium Carbonate | 5.5 |
| Sodium Bicarbonate | 5.4 |
| Mannitol | 32.9 |
| Hydroxypropyl Cellulose | 1.4 |
| Total | 100.0 |

3B. Preparation of Intestinally Soluble Prolonged Release Granules 600 g of non-coated granules 3A are placed into a coating apparatus with fluidized bed. The granules are spray coated with 1,667 g of a coating liquid having the following composition according to a conventional method to produce long-acting granules.

The amount of the coat is about 20% based on the weight of the non-coated granules.

| Component | % by Weight |
|---|---|
| Methacrylic Acid Copolymer S | 6.5 |
| Glycerine Fatty Acid Ester | 0.5 |
| Talc | 0.2 |
| Ethyl Alcohol | 92.8 |
| Total | 100.0 |

Example 4

4A. Preparation of Non-Coated Granules for Long-Acting Formulations 700 g of 23CPPA, 350 g of potassium carbonate, and 150 g of potassium bicarbonate are mixed and pulverized. The fine powders thus produced are processed to produce spherical granules, using 600 g of purified sucrose that was obtained by shifting through 20-28 mesh as a core, while spraying a solution of 25 g of hydroxypropyl cellulose in 475 g of ethyl alcohol. The granules are then dried for 3 hours at 55° C. These dried granules are then passed through a 14 mesh followed by passage through a 28 mesh. The granules which do not go through the 28 mesh are taken as non-coated granules. The formulation of the non-coated granules is as follows:

| Component | % by weight |
| --- | --- |
| 23CPPA | 38.3 |
| Potassium Carbonate | 19.2 |
| Potassium Bicarbonate | 8.2 |
| Purified Sucrose | 32.9 |
| Hydroxypropyl cellulose | 1.4 |
| Total | 100.0 |

4B. Preparation of Water Insoluble Prolonged Release Granules 600 g of non-coated granules 4A are placed into a coating apparatus with fluidized bed. The granules are spray coated with 900 g of a coating liquid having the following composition according to a conventional method to produce long-acting granules. The amount of the coat was about 6% based on the weight of the non-coated granules.

| Component | % by weight |
| --- | --- |
| Aminoalkyl Methacrylate Copolymer | 3.3 |
| Polyvinylpyrolidone | 0.5 |
| Talc | 0.2 |
| Ethyl Alcohol | 96.0 |
| Total | 100.0 |

Example 5

5A. Preparation of Non-Coated Granules for Long-Acting Formulations

To mixed powders of 700 g of 23CPPA, 350 g of sodium carbonate, 100 g of sodium bicarbonate, 600 g of lactose, and 400 g of purified sucrose, is added a solution of 60 g of hydroxypropyl cellulose in 540 g of purified water, and the mixture is kneaded. The kneaded product is processed to produce spherical granules using a cylindrical granulator. The granules are then dried for 3 hours at 55° C. These dried granules are then passed through a 16 mesh followed by passage through a 30 mesh. The granules which do not go through the 30 mesh are taken as non-coated granules. The formulation of the non-coated granules is as follows:

| Component | % by weight |
| --- | --- |
| 23CPPA | 31.8 |
| Sodium Carbonate | 15.8 |
| Sodium Bicarbonate | 4.5 |
| Lactose | 27.1 |
| Purified Sucrose | 18.1 |
| Hydroxypropyl Cellulose | 2.7 |
| Total | 100.0 |

5B. Preparation of Intestinally Soluble Prolonged Release Granules 500 g of non-coated granules 5A are placed into a coating apparatus with fluidized bed. The granules are spray coated with 2,083 g of a coating liquid having the following composition according to a conventional method to produce long-acting granules. The amount of the coat is about 30% based on the weight of the non-coated granules.

| Component | % by weight |
| --- | --- |
| Methacrylic Acid Copolymer L | 6.5 |
| Glycerine Fatty Acid Ester | 0.5 |
| Talc | 0.2 |
| Ethyl Alcohol | 98.8 |
| Total | 100.0 |

Example 6

23CPPA dissolution from the long-acting granules according to Example 3B and the comparator non-coated granules according to Example 3A, with measurement by the rotating paddle method (U.S. Pharmacopeia, 29th Edition) using a buffer at pH 4.5. Suppressed release of 23CPPA from the long-acting granules as compared with the non-coated granules is demonstrated.

Dissolution of 23CPPA Granules:

| Granule | pH | %23 CPPA Released:Time (hours) | | | | | | | |
| --- | --- | --- | --- | --- | --- | --- | --- | --- | --- |
| | | 0 | 1 | 2 | 4 | 8 | 12 | 18 | 24 |
| 3A | 4.5 | 0 | 53 | 77 | 100 | 100 | 100 | 100 | 100 |
| 3B | 4.5 | 0 | 2 | 5 | 9 | 17 | 28 | 39 | 51 |

Example 7

23CPPA dissolution from the long-acting granules according to Example 4B and the comparator non-coated granules according to Example 4A, with measurement by the rotating paddle method (U.S. Pharmacopeia, 29th Edition) using a buffer at pH 6.8. Suppressed release of 23CPPA from the long-acting granules as compared with the non-coated granules is demonstrated.

Dissolution of 23CPPA Granules:

| Granule | pH | %23 CPPA Released:Time (hours) | | | | | | | |
|---|---|---|---|---|---|---|---|---|---|
| | | 0 | 1 | 2 | 4 | 8 | 12 | 18 | 24 |
| 4A | 6.8 | 0 | 85 | 100 | 100 | 100 | 100 | 100 | 100 |
| 4B | 6.8 | 0 | 5 | 11 | 23 | 42 | 64 | 90 | 100 |

Example 8

23CPPA concentrations in Beagle dogs receiving comparator non-coated granules 5A containing 48 mg of 23CPPA and long-acting granules 5B according to Example 5 containing 50 mg 23CPPA. Prolonged plasma concentration of the long-acting granules as compared with the non-coated granules is demonstrated.

Pharmacokinetics in Beagle Dogs:

| Granule | Plasma 23CPPA (ng/ml):Time (hours): | | | | | | | | |
|---|---|---|---|---|---|---|---|---|---|
| | 0 | 0.5 | 1 | 2 | 4 | 8 | 12 | 18 | 24 |
| 5A | 0 | 5770 | 12130 | 6520 | 3260 | 830 | 220 | 50 | 0 |
| 5B | 0 | 80 | 340 | 1120 | 4230 | 3460 | 2300 | 850 | 0 |

Example 9

Oral Bioavailability of 23CPPA

The bioavailability of 23CPPA was ascertained in male rats given a single dose of 23CPPA by the oral route (30 mg/kg) or by the intravenous route (3.0 mg/kg). Timed samples of blood were collected before and after dosing, and plasma concentrations of the compound were determined with liquid chromatography mass spectrometry (LC-MS-MS) analysis. Oral bioavailability, calculated from the plasma concentrations after oral versus intravenous administration, was 85%, indicating that the drug is absorbed from the gastrointestinal tract and enters the circulation for systemic delivery.

Example 10

Reaction Rate of Nonenzymatic Glycation of Albumin

Serum, plasma or purified human albumin was incubated with 10 to 40 mM glucose for one to nine days, and samples were assayed for albumin containing Amadori glucose adducts (Amadori-modified glycated albumin; AGA). At baseline, AGA represented approximately 0.6% of total albumin and steadily increased over the ensuing study period with end-of-study levels dependent on glucose concentration. The slopes of the lines for change with time of percent AGA were used to calculate the rate of formation of AGA which was 0.005 to 0.008 percent.

Non-Enzymatic Glycation of Albumin

| Sample | Glucose | % AGA | Slope | Rate (% mM glucose/day) |
|---|---|---|---|---|
| Plasma | 10 mM | 1.1 | 0.052 | 0.052 |
| | 20 mM | 1.9 | 0.136 | 0.0068 |
| | 40 mM | 3.3 | 0.3070 | 0.0076 |
| Albumin | 10 mM | 0.8 | 0.0771 | 0.0077 |
| | 20 mM | 1.4 | 0.1471 | 0.0074 |
| | 40 mM | 2.9 | 0.3137 | 0.0078 |

Example 11

A 23CPPA core tablet is prepared having the following formulation:

| | wt. % | mg/tablet |
|---|---|---|
| 23CPPA potassium | 60.0 | 1000.00 |
| anhydrous lactose, NF | 5.0 | 83.33 |
| hydroxypropyl methylcellulose, USP | 28.8 | 480.00 |
| sodium citrate, USP | 5.0 | 83.33 |
| colloidal silicon dioxide | 0.2 | 3.33 |
| magnesium stearate, NF | 1.0 | 16.67 |

All of the ingredients except the magnesium stearate are passed through a #30 mesh (USSS) mesh screen and are blended for 10 minutes prior to adding the magnesium stearate which has been passed through a #40 mesh screen. Thereafter the combined ingredients are blended for 60 minutes and compressed tablets are prepared with a Manesty Betapress using a 0.379" flat face beveled edge punch and die set.

The coating suspension is prepared at 3% coating level for a 10.5 Kg. batch by blending:

| | wt. % | mg/tablet | Kg/batch |
|---|---|---|---|
| Hydroxypropyl methyl cellulose phthalate, NF | 2.07 | 4.91 | 0.217 |
| Hydroxypropyl cellulose, NF | 0.10 | 0.24 | 0.011 |
| Talc, USP | 0.62 | 1.47 | 0.065 |
| Acetyl tributyl citrate | 0.21 | 0.50 | 0.022 |
| Isopropyl alcohol, USP | * | * | 4.19 |
| Purified water, USP | * | * | 1.796 |

* evaporates during processing

All of the ingredients of the coating suspension are dispersed in the purified water and the isopropyl alcohol.

The core tablets are coated in a pan coating apparatus (Labcoat II, O'Hara Manufacturing Ltd.) to form the enteric coated tablets.

Example 12

Dissolution of Formulated 23CPPA

Dissolution profile of a 1000 mg 23CPPA tablet, made according to Example 11 of the present application, in simulated gastric fluid (SGF), at pH 4.2, at pH 6.2 and in simulated intestinal fluid (SIF). The figure (FIG. 1) shows release rate profiles of the 23CPPA formulation in various pH dissolution media, which are essentially zero order release rates, and demonstrates very limited solubility of once-a-day 23CPPA in simulated gastric fluid (SGF) and/or at pH 4.2, with less than 15% of 23CPPA released at 4 hours.

Example 13

Pharmacokinetics of Formulated 23CPPA

Figure 2:
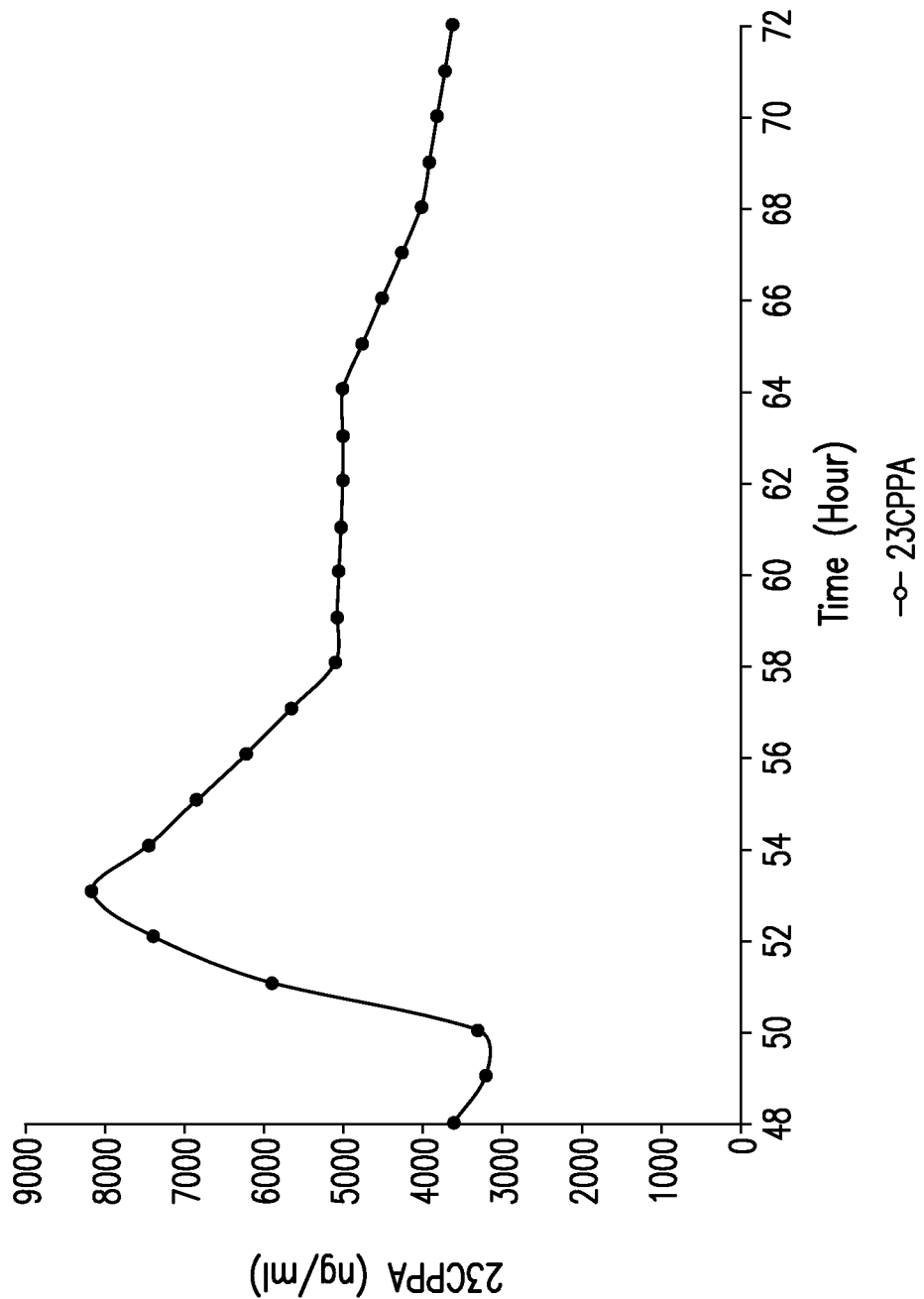
FIG. 2 is a graph plotting 23CPPA plasma levels versus time following oral administration once a day for four consecutive days of 23CPPA prepared according to Example 11 of the present invention and as described and used in the test illustrated in FIG. 1.

The figure (FIG. 2) shows pharmacokinetic profile plotting of 23CPPA plasma levels versus time following oral administration once a day for four consecutive days of 23CPPA prepared according to Example 11 of the present invention and as described and used in the test illustrated in Example 12 and FIG. 1. The figure shows a 24 hours period from day 2 to 3 (48 to 72 hours) after initiation of the once a day oral administration.

While certain preferred and alternative embodiments of the invention have been set forth for purposes of disclosing the invention, modifications and variations to the disclosed embodiments of the present invention are possible in light of the above teachings and may occur to those who are skilled in the art. It is therefore to be understood that the invention may be practiced otherwise than as specifically described herein. Accordingly, the appended claims are intended to cover all embodiments of the invention and modifications thereof which do not depart from the spirit and scope of the invention.

What is claimed is:

1. A once-a-day 2-(3-chlorophenylamino) phenylacetic acid dosage formulation which comprises:
   (a) a core element comprising a compressed tablet containing a therapeutic dose of 2-(3-chlorophenylamino) phenylacetic acid blended with a solubility modulating substance consisting of at least one hydrogel forming polymer in an amount effective to control the release of said 2-(3-chlorophenylamino) phenylacetic acid to provide a therapeutic level over a period of about 24 hours; and
   (b) an enteric coating which is placed around said core element, wherein said dosage formulation controls the release of said 2-(3-chlorophenylamino) phenylacetic acid to provide a therapeutic level meeting drug-to-target relationships according to the albumin concentration in the blood and the rate of reaction between free glucose and albumin over a period of about 24 hours.

2. A once-a-day controlled release 2-(3-chlorophenylamino) phenylacetic acid formulation as defined in claim 1 wherein the enteric coating polymeric material is selected from the group consisting of hydroxypropyl methylcellulose phthalate, shellac, methacrylic acid copolymers and cellulose acetate phthalate.

3. A once-a-day controlled release 2-(3-chlorophenylamino) phenylacetic acid formulation as defined in claim 1 wherein the enteric coating polymeric material on the core tablet contains a plasticizer.

4. A once-a-day 2-(3-chlorophenylamino) phenylacetic acid dosage formulation which comprises:
   (a) a core element comprising a compressed tablet containing a therapeutic dose of 2-(3-chlorophenylamino) phenylacetic acid blended with a solubility modulating substance consisting of at least one hydrogel forming polymer in an amount effective to control the release of said 2-(3-chlorophenylamino) phenylacetic acid to provide a therapeutic level over a period of about 24 hours; and
   (b) an enteric coating which is placed around said core element;
wherein the formulation follows a zero order rate of release from about one hour to about sixteen hours.

5. A once-a-day 2-(3-chlorophenylamino) phenylacetic acid dosage formulation which comprises:
   (a) a core element comprising a compressed tablet containing a therapeutic dose of 2-(3-chlorophenylamino) phenylacetic acid blended with a solubility modulating substance consisting of at least one hydrogel forming polymer in an amount effective to control the release of said 2-(3-chlorophenylamino) phenylacetic acid to provide a therapeutic level over a period of about 24 hours; and
   (b) an enteric coating which is placed around said core element;
wherein the formulation has a dissolution rate, in 1000 ml of simulated intestinal fluid, when measured in a USP 23 apparatus, Type 2, at 37° C. and 100 rpm, measured by using a spectrophotometer at a wavelength of 283 nm, which substantially corresponds to the following:
   (a) from 0 to 35% of total 2-(3-chlorophenylamino) phenylacetic acid is released after one hour;
   (b) from 40 to 65% of total 2-(3-chlorophenylamino) phenylacetic acid is released after 5 hours;
   (c) from 65 to 85% of total 2-(3-chlorophenylamino) phenylacetic acid is released after 10 hours;
   (d) not less than 70% of total 2-(3-chlorophenylamino) phenylacetic acid is released after sixteen hours; and
   (e) not less than 80% of total 2-(3-chlorophenylamino) phenylacetic acid is released after twenty four hours.

6. A once-a-day controlled release 2-(3-chlorophenylamino) phenylacetic acid formulation according to claim 1 that provides delivery of therapeutically effective concentrations of 2-(3-chlorophenylamino) phenylacetic acid during the period of time that the drug is in the circulation.

7. A once-a-day controlled release 2-(3-chlorophenylamino) phenylacetic acid formulation as defined in claim 1 wherein the solubility modulating substance is hydroxypropyl methylcellulose.

8. A once-a-day controlled release 2-(3-chlorophenylamino) phenylacetic acid formulation as defined in claim 2 wherein the enteric coating polymeric material is hydroxypropyl methylcellulose phthalate.

9. A once-a-day controlled release 2-(3-chlorophenylamino) phenylacetic acid formulation as defined in claim 3 wherein the plasticizer is acetyl tributyl citrate.

10. A once-a-day controlled release 2-(3-chlorophenylamino) phenylacetic acid formulation as defined in claim 1 wherein the hydrogel forming polymer is selected from the group consisting of hydroxypropyl methylcellulose, hydroxypropyl cellulose, hydroxyethyl cellulose, sodium alginate, xanthan gum, and carbomer.

11. A method of treating a patient with a diabetes-associated complication, without influence on glycemic status, comprising administering to the patient once-daily the formulation of claim 1 in an amount effective to therapeutically treat the diabetes-associated disorder.

* * * * *